(12) United States Patent
Reilly

(10) Patent No.: US 8,475,042 B1
(45) Date of Patent: Jul. 2, 2013

(54) THERMAL SHIELD SYSTEM FOR HIGH TEMPERATURE ENVIRONMENT XRF METROLOGY TOOLS

(75) Inventor: Francis Reilly, Bayport, NY (US)

(73) Assignee: Ceres Technologies, Inc., Saugerties, NY (US)

( * ) Notice: Subject to any disclaimer, the term of this patent is extended or adjusted under 35 U.S.C. 154(b) by 200 days.

(21) Appl. No.: 12/925,366

(22) Filed: Oct. 20, 2010

Related U.S. Application Data

(60) Provisional application No. 61/279,433, filed on Oct. 21, 2009.

(51) Int. Cl.
*H05G 1/00* (2006.01)
(52) U.S. Cl.
USPC .............................. 378/204; 378/44; 378/142
(58) Field of Classification Search
USPC ........................................... 378/44, 142, 204
See application file for complete search history.

(56) References Cited

U.S. PATENT DOCUMENTS 2,618,321 A * 11/1952 Spies, Jr. ........................ 239/128

* cited by examiner

*Primary Examiner* — Jurie Yun

(57) ABSTRACT

A thermal shield for an XRF measurement tool is formed from a heat shield and a heat shield cowling. These components protect the X-ray head assembly that includes the x-ray generation and detection columns and the head control electronics, communications and cooling systems. The heat shield is directly below the X-ray head, parallel to the x-ray head plane and plane of the PV substrate, and perpendicular to the primary beam output from the x-ray head. The heat shield is fabricated of machined copper with several ports machined through the shield. These ports provide a path for primary beam x-rays through the heat shield and for the return of fluoresced X-rays from the PV substrate back to the detector in the X-ray head, while preventing damage to the X-ray head due to the heat emitted from the PV substrate.

13 Claims, 4 Drawing Sheets

THERMAL SHIELD SYSTEM FOR HIGH TEMPERATURE ENVIRONMENT XRF METROLOGY TOOLS

CROSS-REFERENCE TO RELATED APPLICATIONS

This application claims priority under 35 USC 119(e) of U.S. Provisional Patent Application Ser. No. 61/279,433, filed on Oct. 21, 2009.

BACKGROUND OF THE INVENTION

The present invention relates to a thermal shield system for high temperature environment XRF metrology tools. In particular, the invention relates to a specialized housing that protects the XRF metrology tool from the heat given off by the substrate.

X-ray based metrology tools are required to manufacture the active layer in copper indium gallium diselenide photovoltaic cells (CIGS PV cells) cells that convert sunlight to electricity. Atmospheric-based processes that deposit these films must be controlled directly after film deposition to ensure acceptable commercial output. At this process point, the substrate materials are extremely hot (100-300° C.). Waiting for these substrate materials to cool for film analysis is impractical, since it would disrupt and negatively impact the PV panel performance and would adversely affect plant capacity. As a result, XRF analysis of the integrity of the film stack (thickness and composition determination) must be performed on materials that are extremely hot. This allows adjustment to the deposition process to maintain engineered film tolerances. Atmospheric CIGS PV manufacture requires real-time information that allows correction of process deviation immediately without allowing substrates to cool. XRF measurement data is required to manage yield and optimize conversion efficiencies for maximum resultant electric output of the PV material.

However, X-ray based metrology tools are expensive and delicate instruments that will not survive in a high temperature (100-300° C.) atmospheric processing environments typical of CIGS and related film deposition processes. The XRF tool must reside very close (within less than 1 inch) of the hot substrate, and perform constant uninterrupted measurements since plant operations are 24 hours a day/7 days a week and 365 days a year. It is thus necessary to ensure tool survival and measurement capability and stability protection from these harsh conditions while simultaneously allowing XRF measurement.

SUMMARY OF THE INVENTION

It is therefore an object of the invention to provide a system that protects the XRF measurement tool from the heat of the substrate, while allowing the tool to perform the required measurements on the hot substrate.

This object is accomplished by a thermal shield for an XRF measurement tool that comprises a heat shield element and a heat shield cowling. These components protect the X-ray head, which is the subassembly that generates and detects X-rays. The x-ray head assembly includes the x-ray generation and detection columns and the head control electronics, communications and cooling systems. The heat shield is directly below the X-ray head, parallel to the x-ray head plane and plane of the PV substrate, and perpendicular to the primary beam output from the x-ray head. The heat shield is fabricated of machined copper with several ports machined through the shield. These ports provide a path for primary beam x-rays through the heat shield and for the return of fluoresced X-rays from the PV substrate back to the detector in the X-ray head. Copper is used to deflect the infrared radiation that is emitted from the PV substrate. The copper heat shield is manufactured to be very thin, as a thick layer would absorb excessive heat from the substrate.

The location of the detector port that allows X-rays to make their way back to the detector, and the geometric relation of the PV panel, thermal heat shield and X-ray head minimizes or prevents IR light from striking the detector by impinging the line of site path of IR emitted from the PV panel.

In addition, the thermal heat shield prevents heated air from impinging on the x-ray head. This is accomplished by utilizing mechanics and thermal sink. The copper heat shield is designed to block most of the convected air flow away from the head and up towards the heat shield cowling through use of geometry.

Specifically, the flat surface makes the heated air move out and away from the heat shield ports, around the side of the cowling. The geometrically strategically positioned ports in the heat shield coupled with an internal head mounted air based cooling system prevents hot air from moving through these holes by creating an air curtain across the holes above and on the cool side of the heat shield (i.e., head side). The fan inside the cowling pushes cool air down and around the head, with some being blown outward through the ports, preventing any inflow of hot air from the substrate. In addition, there can be an air flow assist comprised of two additional fans mounted above the head/shield assembly at lateral positions on either side of the X-ray head. These facilitate additional air movement up and away from the entire assembly.

The heat shield cowling provides mechanical air flow direction and also prevents wrap-around of convected air. The cowling is fabricated out of aluminum, since the IR requirements are relaxed due to the fact that the cowling is parallel to the ray geometry of the IR path and since it retains heat less than the copper and is light weight.

This system (X-ray head, thermal heat shield and heat shield cowling) enables XRF measurements to be performed with the X- ray head remaining in an air environment at extremely high temperatures that would otherwise damage the metrology tool and prevent film process control. The system according to the invention protects the X-ray head for panel and web temperatures of up to 300° C. This capability substantially reduces panel dwell times, improves throughput and allows one to maintain process tack time while simultaneously obtaining real time XRF measurement data for CIGS process films.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE EMBODIMENTS

Figure 1:
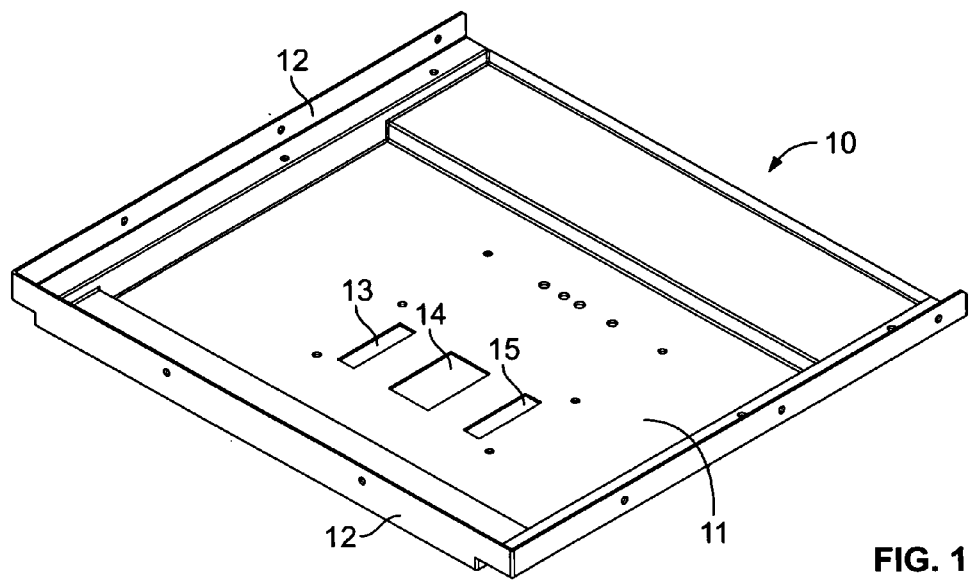
FIG. 1 shows a perspective view of the heat shield element for use in the system according to the invention.
Figure 2:
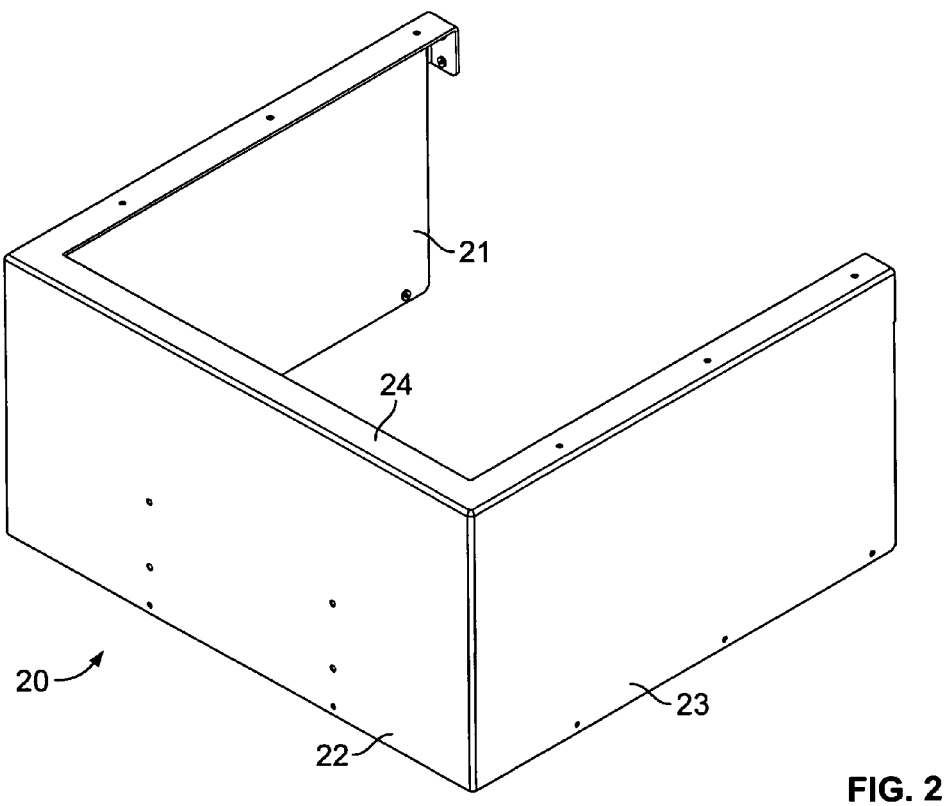
FIG. 2 shows a perspective view of the cowling for use in the system according to the invention.
Figure 3:
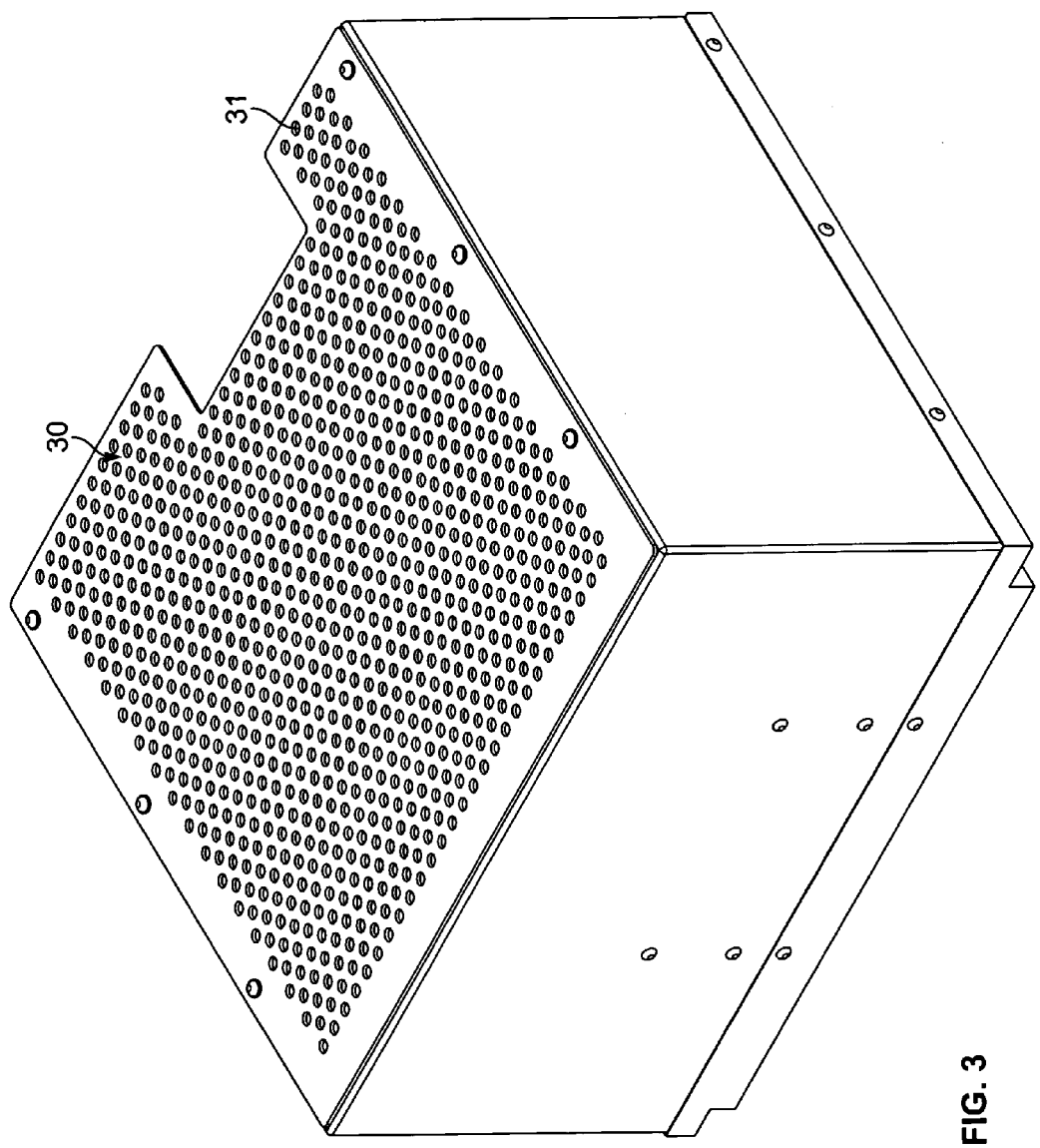
FIG. 3 shows a perspective view of the heat shield, cowling and cover according to the invention.

Referring now in detail to the drawings and, in particular, FIGS. 1-3 show the heat shield assembly according to the invention. Heat shield assembly consists of copper heat shield element 10, having a flat bottom 11, side flanges 12 and apertures 13, 14 and 15. Cowling 20 is assembled on flanges 12 to create a box-like structure. Cowling 20 consists of side walls 21, 22, 23 and top flange 24, which surrounds the top of the side walls. A cover 30 can be placed on the top of cowling 20, to protect the x-ray head placed inside. Cover 30 has a plurality of ventilation holes 31 to allow for air flow into and out of the interior of cowling 20 and heat shield element 10. All of the pieces, i.e., the heat shield element 10, cowling 20 and cover 30, can be bolted together, or held together by any other suitable means.

Figure 4:
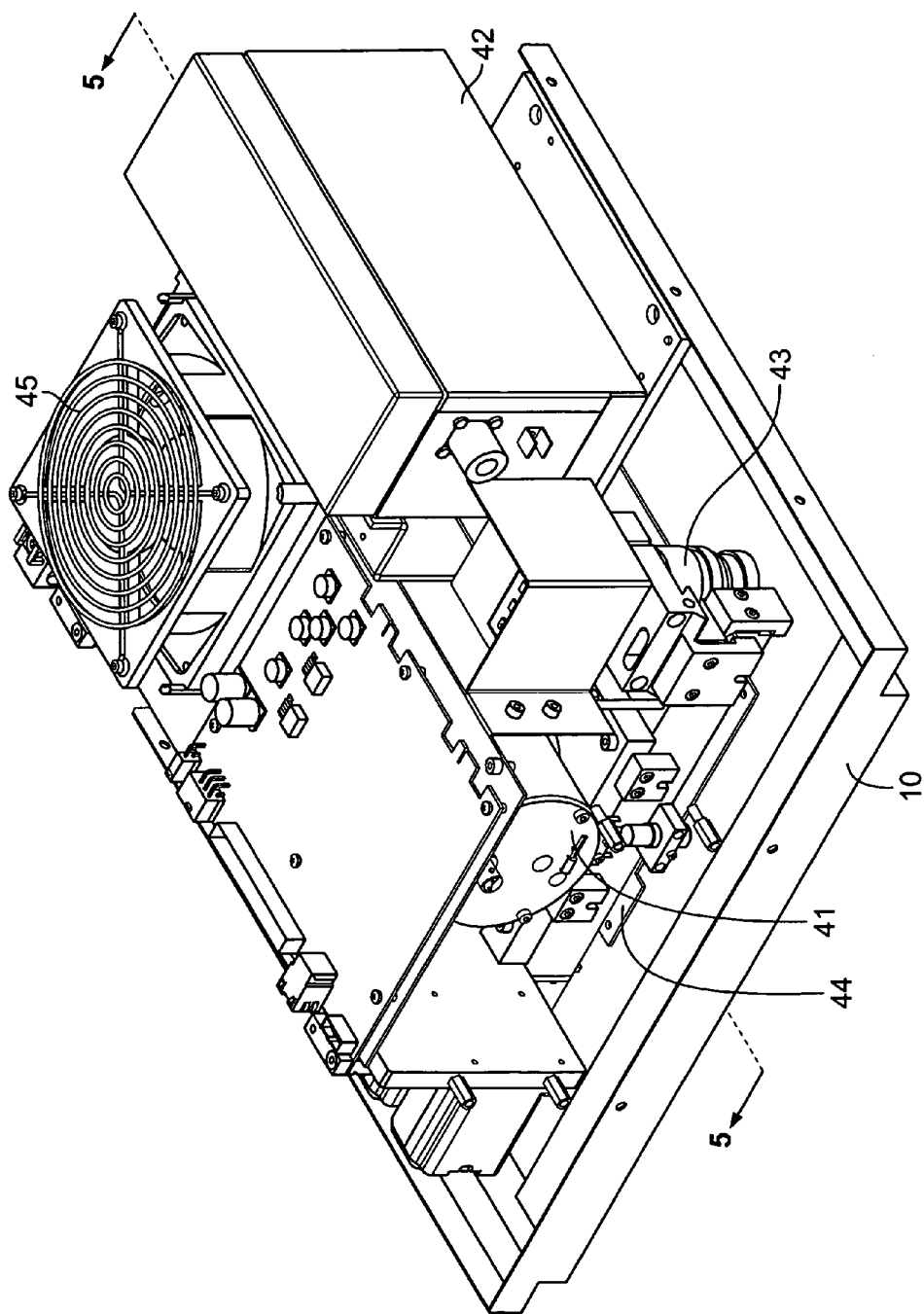
FIG. 4 shows a perspective view of the X-ray head mounted on the heat shield according to the invention.

FIG. 4 shows a view of the X-ray metrology machine 40 resting on heat shield element 10. Machine 40 consists of X-ray head 41, power element 42, camera 43, light assembly 44, and fan 45.

Figure 5:
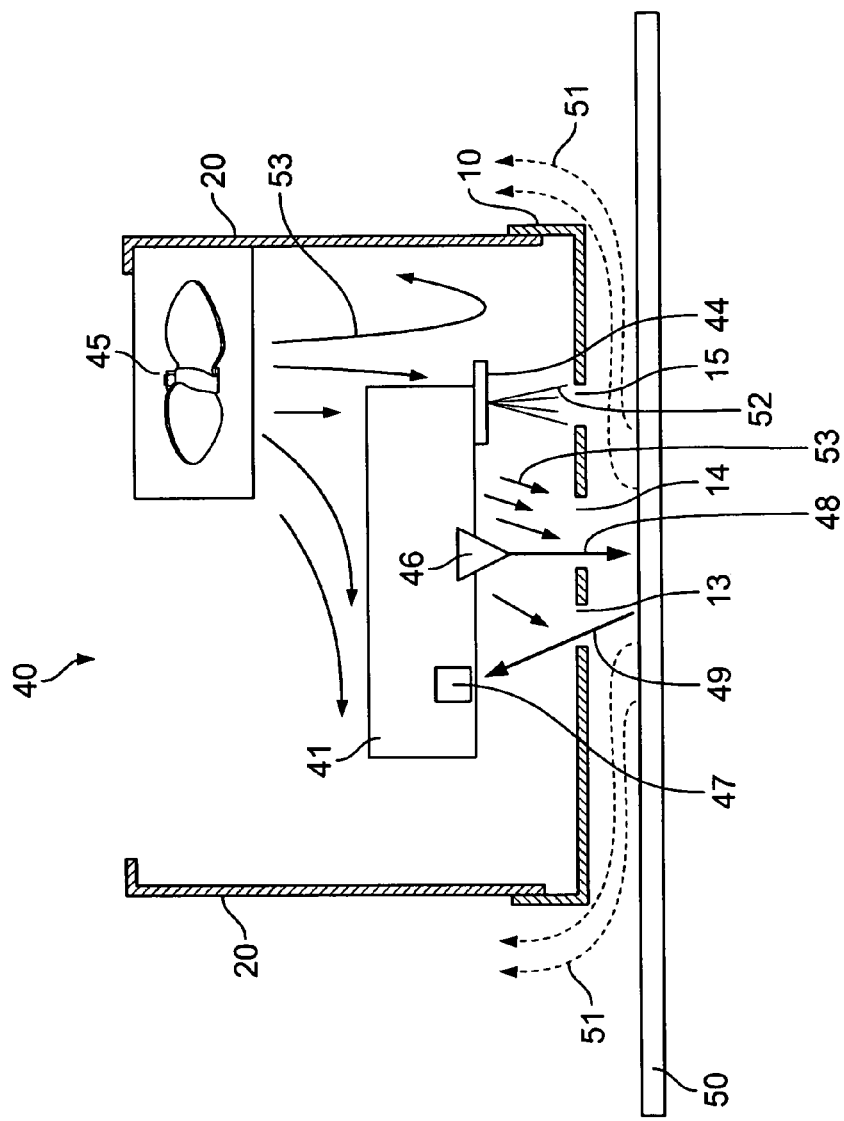
FIG. 5 shows a partial cross-sectional view of the system according to the invention and the air flow properties of the heat shield and cowling.

A simplified schematic cross-section of the machine and heat shield assembly positioned over a substrate are shown in FIG. 5. Here, X-rays 48 generated by generator 46 of X-ray head 41 pass through aperture 14 to hit substrate 50. Aperture 14 is positioned directly under generator 46 so that the X-rays have a perpendicular path to substrate 50. X-rays 49 that fluoresce off of substrate 50 then pass back through heat shield element 10 via aperture 13 to reach detector 47 on X-ray head 41. Aperture 13 is positioned offset from detector 47 so that the X-rays that reach detector 47 travel in a direction that is not perpendicular to a plane of heat shield element 10. This prevents IR radiation from traveling perpendicularly through aperture 13 to reach detector 47. Information from the fluoresced X-rays is then sent from detector 47 to a control station (not shown) for analysis. To aid in visual inspection, light assembly 44, which contains an LED, emits light that passes through aperture 15 in heat shield element 10 to reach substrate 50.

Cooling of X-ray metrology machine 40 takes place by several different ways. First, cool air is pulled from above via fan 45 and passed downward (see arrows 53) around X-ray head. Some of this cooler air also passes out of apertures 13, 14, 15, thus creating a barrier to heat from substrate 50 entering through these apertures. In addition, heat from substrate 50 (indicated by arrows 51) passes around heat shield element 10 and up along cowling 20 and cannot penetrate heat shield element 10, as convection forces cause it to move linearly along the cowling and away from X-ray head 41. Additional fans (not shown) can be positioned above the entire assembly to keep the air moving.

This way, X-ray head 41 is protected from heat and IR radiation given off by substrate 50, which would otherwise damage X-ray head 41. The apertures in head shield element 10 allow for full penetration of the X-rays for analysis, but due to fan 45, the position of apertures 13, 14, 15 and the shape of heat shield element 10 and cowling 20, the heat and radiation cannot enter through these apertures and damage X-ray head 41. Preferably, the entire assembly is positioned approximately 1 inch above the substrate 50, so that accurate measurements may be taken. Heat shield element 10 and cowling 20 protect X-ray metrology machine 40 from the heat generated by substrate 50, even from this distance and even when the temperature of substrate 50 approaches 300° C.

Accordingly, while only a few embodiments of the present invention have been shown and described, it is obvious that many changes and modifications may be made thereunto without departing from the spirit and scope of the invention.

What is claimed is:

1. A heat shield for an XRF metrology tool, comprising:
    a heat shield element and having a base, wherein apertures for X-rays are formed into the base; and
    a cowling surrounding the heat shield element, said cowling having at least three side walls and being connected to the heat shield element to form an interior cavity,
    wherein at least one of said apertures is arranged to allow X-rays from the XRF metrology tool to pass unobstructed therethrough.

2. The heat shield according to claim 1, wherein the heat shield has upwardly extending flanges surrounding a perimeter of the base, the flanges being attached to the cowling.

3. The heat shield according to claim 1, wherein the cowling is formed from aluminum.

4. The heat shield according to claim 1, wherein the heat shield element is formed from copper.

5. The heat shield according to claim 1, further comprising at least one fan disposed within the cavity.

6. The heat shield according to claim 1, wherein there are two apertures for X-rays and an additional aperture arranged to allow for light to pass through.

7. A system for performing X-ray fluorescence metrology on a substrate, comprising:
    a heat shield element having a base with apertures forming X-ray ports;
    a cowling surrounding the heat shield element, said cowling having at least three side walls and being connected to the heat shield element to form an interior cavity; and
    an X-ray metrology machine having an X-ray generator and a detector, said X-ray metrology machine being positioned in the cavity such that when the system is positioned above a substrate, X-rays emitted from the generator pass through one of the apertures, and X-rays fluoresced from the substrate pass through another of said apertures to the detector.

8. The system according to claim 7, further comprising at least one fan disposed in the cavity.

9. The system according to claim 8, wherein the fan is positioned above the X-ray metrology machine and blows air downward, around the X-ray metrology machine and through the apertures in the heat shield element.

10. The system according to claim 7, wherein the heat shield element is formed from copper.

11. The system according to claim 7, wherein the cowling is formed from aluminum.

12. The system according to claim 7, further comprising a light assembly connected to the X-ray metrology machine, wherein light from the light assembly passes through one of the apertures in the heat shield element.

13. The system according to claim 7, wherein the aperture through which fluoresced X-rays pass to reach the detector is positioned offset from the detector so that the X-rays that reach the detector travel in a direction that is not perpendicular to a plane of the heat shield element.

* * * * *